United States Patent
Storbeck et al.

(10) Patent No.: US 6,928,892 B2
(45) Date of Patent: Aug. 16, 2005

(54) CONFIGURATION FOR DETERMINING A CONCENTRATION OF CONTAMINATING PARTICLES IN A LOADING AND UNLOADING CHAMBER OF AN APPLIANCE FOR PROCESSING AT LEAST ONE DISK-LIKE OBJECT

(75) Inventors: Olaf Storbeck, Dresden (DE); Ralph Trunk, Bischberg (DE); Lothar Pfitzner, Erlangen (DE); Claus Schneider, Bubenreuth (DE)

(73) Assignees: Infineon Technologies AG, Munich (DE); Fraunhofer Gesellschaft zur Foerderung der Angewandten Forschung E.V., Munich (DE)

( * ) Notice: Subject to any disclaimer, the term of this patent is extended or adjusted under 35 U.S.C. 154(b) by 366 days.

(21) Appl. No.: 10/233,901

(22) Filed: Sep. 3, 2002

(65) Prior Publication Data

US 2003/0047012 A1 Mar. 13, 2003

(30) Foreign Application Priority Data

Sep. 3, 2001 (DE) .......................................... 101 43 074

(51) Int. Cl.$^7$ ............................................. G01N 15/06
(52) U.S. Cl. .................................................... 73/865.8
(58) Field of Search ........................ 73/864.73, 864.81, 73/865.5, 865.8; 356/437, 440

(56) References Cited

U.S. PATENT DOCUMENTS 6,303,398 B1 * 10/2001 Goerigk ........................ 438/14

FOREIGN PATENT DOCUMENTS

| JP | 05 306 988 A | 11/1993 |
| JP | 08 316 115 A | 11/1996 |
| JP | 2000 019 095 A | 1/2000 |

* cited by examiner

*Primary Examiner*—Robert Raevis
(74) *Attorney, Agent, or Firm*—Laurence A. Greenberg; Werner H. Stemer; Ralph E. Locher

(57) ABSTRACT

A configuration for measuring the concentration of contaminating particles at high time resolution in the mini environments of loading and unloading chambers of processing appliances in semiconductor fabrication includes a probe, a movement unit for the probe, a particle detector, vacuum pump and a control unit. Reaching critical layer thicknesses of disk carriers or boats in ovens, and maladjustments of handling systems for wafers, masks, flat panel displays and other disc-like objects can be detected in terms of the cause and quantified immediately. The movement unit moves the probe to a desired position in the loading and unloading chamber as a reaction to the positioning of the handling system. A method of operating the configuration is also provided.

24 Claims, 3 Drawing Sheets

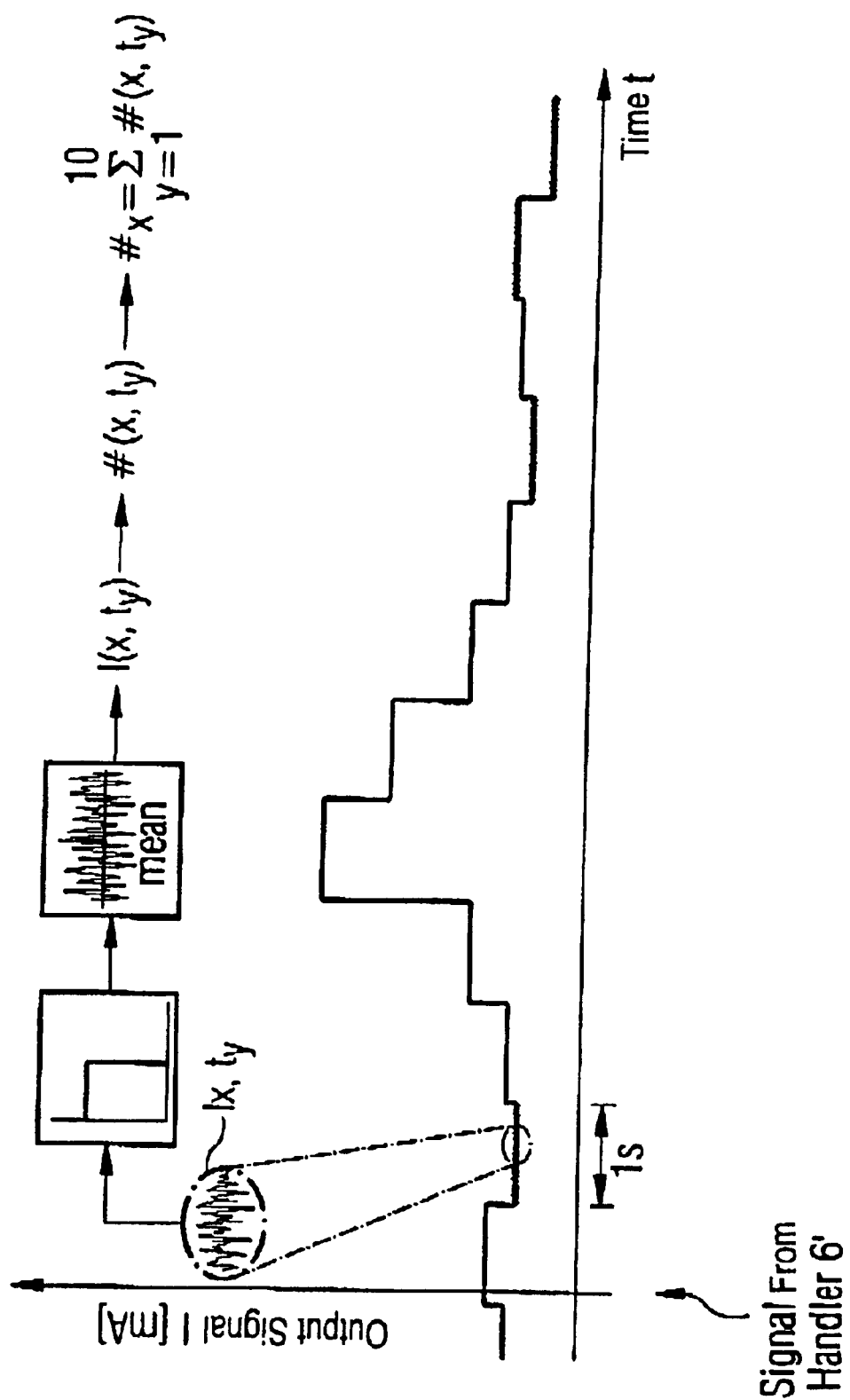

CONFIGURATION FOR DETERMINING A CONCENTRATION OF CONTAMINATING PARTICLES IN A LOADING AND UNLOADING CHAMBER OF AN APPLIANCE FOR PROCESSING AT LEAST ONE DISK-LIKE OBJECT

BACKGROUND OF THE INVENTION

Field of the Invention

The present invention relates to a configuration for determining the concentration of contaminating particles in a loading and unloading chamber of an appliance for processing at least one disk-like object.

In semiconductor fabrication, contamination, for example by particles or foreign substances, constitutes a great risk with the consequences of reducing the quality and total failure of the electronic components. For this reason, the environmental conditions during semiconductor fabrication are kept at the highest possible quality level by filters and by monitoring the physical conditions in the room. That is, the number of contaminating particles per volume element is kept as low as possible.

In order to meet the requirements on structure widths which decrease to an ever increasing extent, a recent development includes much better clean conditions, as compared with the clean room condition (already improved in any case), which are created by using mini environments locally in the processing appliances or in the containers for the semiconductor products (for example, for semiconductor wafers, masks or flat panel displays). As compared with the surrounding clean room, the air in the mini environments has a much lower number of contaminating particles per volume. In particular, in this case, the loading and unloading areas of appliances for processing the disk-like objects are configured as mini environments. This is correspondingly true of appliances for transferring or resorting the products within the transport containers, for example "stockers" or "rake transfer" appliances.

Unfortunately, all moveable parts and components produce contamination, even during fault-free operation. The handling systems for disks and masks in semiconductor fabrication are primarily considered. Unacceptable contamination can occur if maladjustments of the handling systems arise, for example, when disks being loaded or unloaded in a "disk carrier" and "boats" are scraped as a result of an inaccurate adjustment; in the process, layers on the disk or on the disk carrier flake off and become a contamination source. The particles flaked off can be deposited on the same disk or on the disks, which follow or are located underneath and lead to yield losses in the latter.

In particular, disk carriers or boats themselves constitute a serious contamination source. Typically, such disk carriers are used during the deposition of layers on semiconductor disks and wafers. During batch processing, a large number of semiconductor wafers are introduced simultaneously into the insertion spaces (slots), which are normally stacked vertically one above another and, together with the disk carriers, are processed in a processing chamber. Therefore, not only are the semiconductor wafers, but also the disk carriers are coated with the material respectively deposited.

Since the disk carriers are neither cleaned immediately nor replaced following the respective process, the layer thickness accumulates in the course of several processes. As a result of thermal stress or vibration during loading or unloading of the disks, layer particles begin to flake off to an increasing extent after a specific layer thickness has been reached. Thermal stresses are produced in particular, since the disk carriers cool down following oven processing for "layer deposition". The (moving-out) disk carriers still have temperatures of several hundred degrees in the comparatively cool loading and unloading area of the fabrication appliances. A further cause is constituted by sudden pressure changes following low-pressure or high-pressure processes.

Therefore, the loading and unloading areas of processing appliances in semiconductor fabrication are subject to particularly high contamination risk, as a result of particles flaking off, both as a result of increased object handling and as a result of the severe changes in the physical environmental conditions.

The problem is normally monitored by the simultaneous processing of test disks. Following processing by the appliances, the test disks are subjected to a surface inspection to determine particle numbers. If, violations of specified limiting values are determined, a search for the cause can be made and, either maladjustment of the handling systems can be corrected or, if disk carriers are used, they can be replaced.

Further, the following problems may arise: firstly, the processing and examination of test disks leads to a loss of fabrication capacity. Secondly, as a result of the late measurement result, contamination problems that occur suddenly are not detected immediately. In particular, in the case of the problem of the growing "layer thickness" on the disk carriers, the property of the layer material (i.e., "flake off" property) can occur relatively abruptly. In addition, maladjustment of the handling systems can occur suddenly, for example, as a result of external vibrations.

Therefore, in the case of the disk carriers, the accumulated layer thickness is logged and, in order to avoid contamination problems, replacements are made precisely at the point when empirically determined layer thicknesses are reached, at which the flaking of the layer material will supposedly occur. As a result of early flaking (i.e., before the specific layer thickness is reached), a contamination problem arises, which threatens the yield and may be undiscovered. Still, the layer on the disk carriers can be stable, even beyond the determined layer thickness. Nevertheless, since the disk carrier is replaced, a potential "saving" remains unused.

SUMMARY OF THE INVENTION

It is accordingly an object of the invention to provide a configuration for determining a concentration of the contaminating particles in the loading and unloading chamber that overcomes the hereinafore-mentioned disadvantages of the heretofore-known devices of this general type. With the foregoing and other objects in view, there is provided, in accordance with the invention, a configuration that includes at least one probe having an opening for removing at least one gas sample from the loading and unloading chamber (area). A movement unit is disposed in the loading and unloading area. The movement unit is coupled to the probe, which is movable in at least one direction. A particle detector for counting the contaminating particles in the gas sample, a vacuum pump having lines for conveying the gas sample from the probe to the particle detector; and a control unit connected to the particle detector and the movement unit are also provided.

In accordance with another feature of the invention, the particle detector is fitted outside the loading and unloading area.

In accordance with a further feature of the invention, the movement unit contains at least one movement rail and a drive. The probe is movable along the movement rail by the movement drive.

In accordance with an added feature of the invention, the loading and unloading chamber contains a handling appliance for conveying the at least one disk-shaped object.

In accordance with an additional feature of the invention, the handling appliance is a fabrication appliance for performing one of structuring, cleaning, layer-deposition and layer-processing functions of the surface of the disk-shaped object.

In accordance with yet another feature of the invention, the fabrication appliance is an oven for depositing a layer on the surface of the disk-shaped object at high temperatures. accordance with yet a further feature of the invention, the processing appliance is a sorting appliance for resorting disk-shaped objects from a first to a second disk transport container.

In accordance with yet an added feature of the invention, the probe is fixed to the handling appliance for conveying the at least one disk-shaped object.

In accordance with yet an additional feature of the invention, there is provided a disk carrier having sides disposed in the loading and unloading chamber. The disk carrier has at least one insertion space to accommodate the at least one disk-shaped object for a common processing of the objects in the fabrication appliance.

In accordance with again another feature of the invention, the disk carrier includes a configuration of insertion spaces along an axis having an overall extent. The linear movement rail is disposed parallel to the axis when the disk carrier is in one of a loading and unloading positions. The movement rail has a length, which is at least as long as the overall extent of the axis.

In accordance with again a further feature of the invention, the loading and unloading chamber contains a ventilation system having an airflow source for producing a substantially laminar airflow with a substantially reduced concentration of contaminating particles in the loading and unloading area. The probe is fitted to a side of the disk carrier facing away from the airflow source.

In accordance with again an added feature of the invention, the sides include a lee side and the probe is fitted to the lee side of the disk carrier in the loading and unloading chamber.

In accordance with again an additional feature of the invention, the opening of the probe points in the direction of the airflow source for removing an isokinetic gas sample.

In accordance with still another feature of the invention, the disk-shaped object is one of a semiconductor wafer, a mask, a reticle and a flat panel display.

In accordance with still a further feature of the invention, the fabrication appliance has a monitoring unit. The control unit is connected to the monitoring unit of the fabrication appliance for performing a particle number density measurement after a processing activity in the fabrication appliance.

In accordance with still an added feature of the invention, the handling appliance also has a monitoring unit. The control unit is connected to the monitoring unit of the handling appliance for performing a particle density measurement during one of a loading and unloading activity of the handling appliance.

In accordance with still an additional feature of the invention, the movement unit is at least partly covered by a thermally insulating covering for protection against heat.

In accordance with a concomitant of the invention, the movement unit is connected to the vacuum pump via an extraction line for extracting particles produced by abrasion in the movement unit during driving.

With the objects of the invention in view, there is also provided a method of determining a density of contaminating particles in a loading and unloading chamber of a processing appliance for processing at least one disk-shaped object having the steps of providing the disk-shaped object in the loading and unloading chamber, conveying the disk-shaped object with a handling appliance to a first position in the loading and unloading chamber, transmitting the first position to a control unit of a probe, moving the probe based on the first position with a movement unit to a second position in the loading and unloading chamber, removing an air sample from the loading and unloading area with the probe at the second position, conveying the air sample to a particle detector, measuring a number of particles in each volume element of the air sample with the particle detector, comparing the number of particles with a threshold value, and generating a signal based on a result of the comparison.

In accordance with another mode of the invention, the first position is an insertion space for the disk-shaped object in a disk carrier. The second position for the probe lies on a side of the disk carrier facing away from an airflow source in the loading and unloading chamber.

In accordance with a further mode of the invention, the probe is fitted to a lee side of the disk carrier in the loading and unloading chamber.

In accordance with an added mode of the invention, the disk carrier is replaced on the basis of the signal.

In accordance with an additional mode of the invention, the handling apparatus is adjusted on the basis of the signal.

In accordance with yet another mode of the invention, the removing, conveying the air sample and measuring steps are repeated with a period of less than 5 seconds.

In accordance with a concomitant mode of the invention, there is provided the step of generating a starting signal with the handling appliance, when the conveying step of the disk-shaped object is carried out, before a first measurement.

Accordingly, the object is achieved by a configuration and a method for determining the concentration of contaminating particles in a loading and unloading chamber of an appliance for processing at least one disk-like object. The loading and unloading chamber has a concentration of contaminating particles, which is reduced with respect to the surroundings of the processing appliance. The configuration contains at least one probe having an opening for the removal of at least one air sample from the loading and unloading area, a movement unit within the loading and unloading area (to which the probe is fixed such that it can be moved in at least one direction), a particle detector for counting contaminating particles in the air sample, a vacuum pump having lines for conveying the air sample from the probe to the particle detector, and a control unit, which is connected to the particle detector and the movement unit.

Clean room conditions prevail in the loading area of the processing appliance, of disk-like objects (e.g., semiconductor wafers, masks, reticles and flat panel displays). The air in the loading area has a density of contaminating particles, which is considerably reduced with respect to the surroundings of the fabrication appliance (for example, by filtering systems and defined flow conditions). The processing appliance may be a fabrication appliance for structuring the surfaces of the aforementioned products or ovens, etching appliances, layer deposition appliances, CMP apparatus and the like; they may also be "stockers", or sorters and rake transfer appliances, which carry out logistic tasks for disk-distribution or transport within the fabrication facility.

A sample removal probe exists, in the loading and unloading area, which supplies air, extracted from the loading area to a particle detector or particle measuring instrument. In this case, particularly, the particle size number distribution is recorded and output. The respective number can be converted to the volume of the sucked-in aerosol, which results in a particle concentration for the sample. From this, it is possible to draw conclusions about the concentration in a critical volume (for example, directly above the disk surface).

The probe is set up such that it can be moved to a suitable location or a position of interest in the loading and unloading chamber. Between the probe and the particle detector, an aerosol line is disposed, which is operated by a vacuum pump in such a way that the air taken in is conveyed to the particle detector.

In an advantageous embodiment, the particle detector is located outside the loading and unloading area, for example on the outer wall. If the conditions in the loading area correspond to the specifications of the measuring instrument, (for example, in the case of rake transfer appliances) an installation within the space can also be advantageous because of the possible short aerosol lines.

The configuration is operated by a control unit, which, in particular, provides the probe position as a result of movement with the movement unit, together with the measurement by the particle detector and the extraction of air by the vacuum pump. During operation, both individual and continuous measurements, but with discrete time step widths, are possible.

Fitting the probe within the loading and unloading area achieves the advantage that in-situ contamination measurements of particles can be carried out in the mini environment; as a reaction, measures for rectifying the contamination problems can be initiated immediately. The measured data are available immediately. In particular, as a result of monitoring the time-dependent contamination, individual procedures, such as the handling of the disk-like objects or disks (in the following text), can be monitored at high resolution. Therefore, the causes of the contamination can better be determined.

The mobility of the probe furnishes the particular advantage of either being able to remove the air sample to be measured as close as possible to the location of the "supposed cause" or being able to remove it at a location, which is further removed (but, for this purpose, it is adjustably suitable and has defined conditions). Locations of the contamination are, for example, the points of contact between the handling appliances (handling systems below) and the disks, or between the disks and the disk carriers or disk containers.

Since the contamination normally occurs at the instant of the movement, the probe is fitted directly to the handling system, (for example, in the vicinity of the lever or gripper arms of the robots) in an advantageous embodiment of the present invention. Therefore, the probe is moved automatically with the relevant robot arm, and is given a fixed defined distance from the location of contact (and therefore, from the flaking of particles from the disk or disk carrier surface). In this case, the movement unit is the same as the handling system.

In another embodiment, the movement unit is formed by a movement rail with a drive, along which the probe can be moved linearly. Since the handling systems in the mini environment of the loading and unloading area must not be impaired, such a movement unit is preferably located in the edge region of the loading and unloading area. Measurements with test wafers, showed that, in particular, particles with a diameter below 1 $\mu$m predominantly follow the airflows in the mini environment (so, less gravitation). To this end, the movement rail, with the moveable probe fitted to it, is advantageously set up on the lee side of the handling system or disk carrier, in the laminar airflow usually generated in the mini environment. The particles that have flaked off are then carried in the direction of the movement rail with the airflow. The probe can be moved into precisely a position in which the particles arrive at the movement rail, projected in the airflow.

This is particularly advantageous in the case of disk carriers or boats, which are frequently used in ovens, having a height of more than 1.0 m and more than 100 slots or insertion spaces. A probe with such an opening diameter to cover the entire contamination area would be inadequate here due to the flow of 1 cubic foot per minute of air (which is typically used for particle detectors). Instead, a probe of a few centimeters in diameter can be moved to a height of the disk carrier at which a disk is just being loaded or unloaded by the handling system.

In an advantageous embodiment, the probe is oriented in the direction of the airflow source, that is unidirectionally, so that the removal of the air sample can be carried out isokinetically from the main flow.

A further advantage according to the present invention resides in the possible adjustment of the handling system. Monitoring the loading or unloading procedure of a disk by the handling system becomes possible, and, initially, a quality assessment of the adjustment accuracy can be carried out in-situ. In this case, if increased contamination values result, when compared with an empirical value obtained from optimum adjustment, a signal can be output, which initiates readjustment of the handling system. Apart from maladjustments in the "positioning accuracy" of the handling system, speed parameters, which (in the case of erroneous settings) can lead to excessively fast lowering and placement of the disks in a loading position (with the result of flaking of particles) can be corrected. The result of the respective readjustment can be determined immediately by the configuration of the invention.

A particular advantage is produced by the method of the invention through the highly time-resolved particle density measurement. This makes it possible to allocate the cause of contamination to procedures in time and therefore to specific components or parts. A particular advantage is the coupling of the respective monitoring units of the handling system and of the fabrication appliance to the control unit of the configuration, according to the invention. If, for example, handling processes such as the loading and unloading of a disk are signaled by the monitoring unit of the handling system, then, firstly, the probe can be moved to the reported "handling position" by the control unit; secondly, a highly time-resolved particle measurement by the particle detector can be initiated. In this case, the time step is preferably below the duration of the cause of the contamination: for example, the loading of a wafer over about 2–5 seconds in a slot in a boat.

This is similarly true of the fabrication apparatus, for example, when fabrication processes are completed and the process conditions, such as pressure change and temperature drops, are suddenly carried into the mini environment.

Maladjustment is critical not only in the "wafer handler", but also in the "boat handler", for example of an oven. According to the invention, the boat handler is considered as a handling appliance and can likewise be readjusted on the basis of a generated signal.

Other features which are considered as characteristic for the invention are set forth in the appended claims.

Although the invention is illustrated and described herein as embodied in a configuration for determining the concentration of contaminating particles in a loading and unloading chamber of an appliance for processing at least one disk-like object, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 3 is a diagram showing a chronological sequence of a determination of a density of contaminating particles in the loading and unloading area.

DESCRIPTION OF THE PREFERRED EMBODIMENTS

Figure 1:
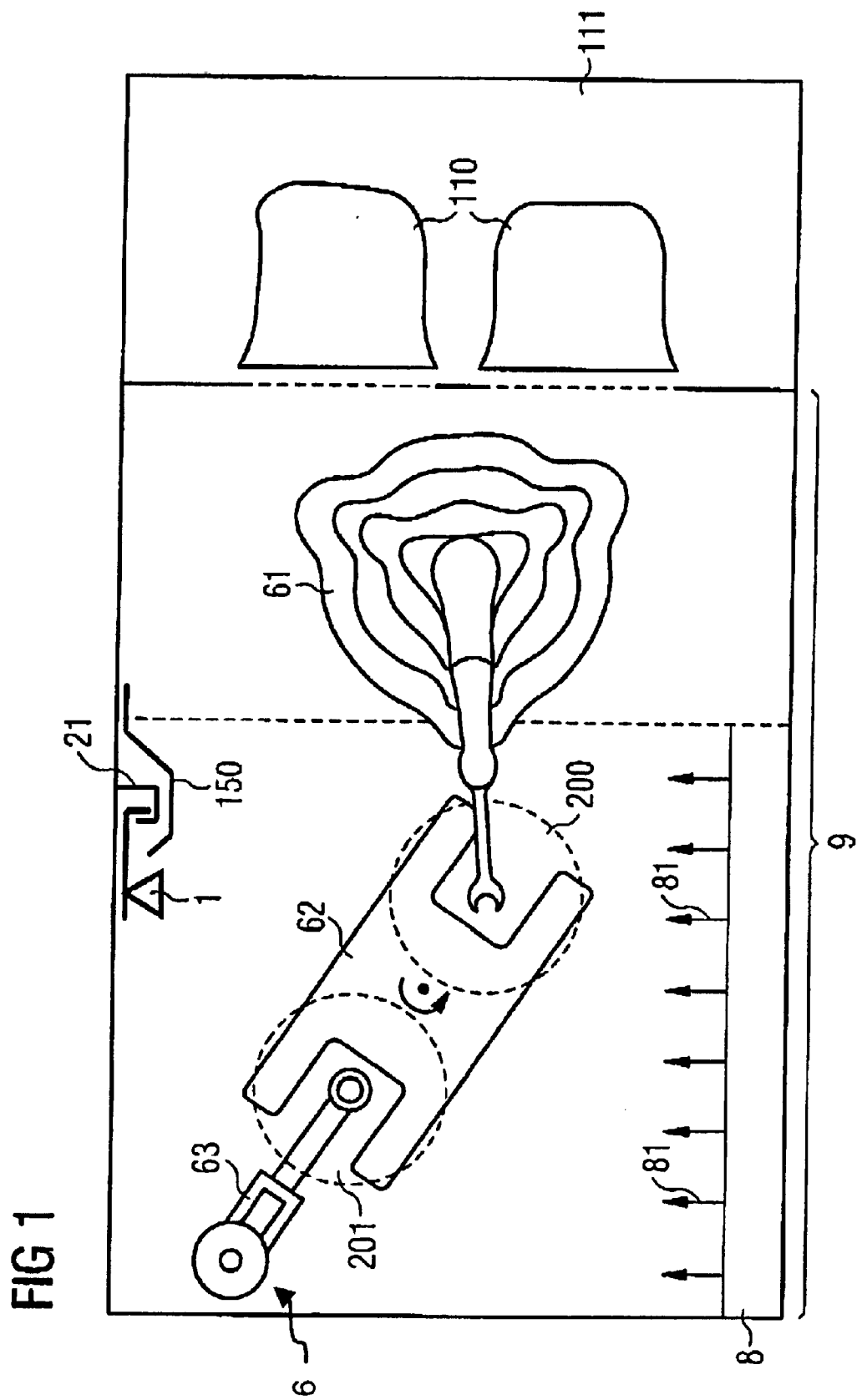
FIG. 1 is a plan view of a cross section of a loading and unloading area of an oven for layer deposition of silicon nitride.

FIG. 1 shows a plan view of a cross section through the loading and unloading area 9 of an oven for the layer deposition of silicon nitride on semiconductor wafers. On the right-hand side, two cartridges or wafer transport containers 110 in the docked state are disposed on the load port 111. The loading and unloading chamber 9 and the wafer transport containers 110 form a common mini environment. The processing chamber of the fabrication appliance 7, that is the actual oven, is located above the plane of the drawing of FIG. 1. Within the loading and unloading area 9, a handling system 6 is disposed, which has a robot 61 with gripper or lever arm, a boat handler 62, and a lever arm 63 for the boats. The robot 61 loads and unloads the semiconductor wafers between the wafer transport containers 110 and the boat 200. The boat 200, which is about 1.10 m high and has 118 insertion spaces, is held by a rotatable boat handler 62. The boat 200 contains a circular base plate, with four quartz rods projecting perpendicularly out of the plane of the drawing, and having 118 slots, which are used as insertion spaces.

Once the boat 200 has been loaded with the wafers to be processed, the boat handler 62 rotates through 180° to interchange the boat positions of the boats 200, 201. The boat 201 is in a position from where it can be moved upward into the oven out of the plane of the drawing by the lever arm 63 of the handling system 6.

An airflow source 8, with a filter system for producing a laminar airflow 81, is disposed in the loading and unloading chamber 9 for obtaining the mini environment. At the location of the boat 200, there is disposed (in particular at the instant of loading) a contamination source for particles, which flake off from the wafer surfaces at the level of the insertion space just being loaded. Submicron particles are carried along by the airflow 81, and carried to the probe 1, which is fitted in the loading and unloading chamber 9, on exactly the opposite side. The probe 1 is located on the lee side of the boat 200 in the airflow 81. It is fitted to a cantilever arm such that it can move on a movement rail 21, which likewise projects perpendicularly out of the plane of the drawing.

The boat 201, just processed in the oven, is moved down on the boat handler 62, and, by the aforementioned rotational movement of the boat handler 62, is pivoted into the previous position of the boat 200 that has just been loaded. The boat 201 and the wafers located therein initially have a temperature of 600° C., and cool down in the mini environment. A thermally insulating protection plate 150 protects the movement rail 21 and the associated drive against the action of heat. The cooling boat 201, newly coated with the wafers, (at this instant) likewise constitutes a particular contamination source. As the boat 201 is moved downward out of the oven, a signal is transmitted to the control unit of the probe 1.

Figure 2:
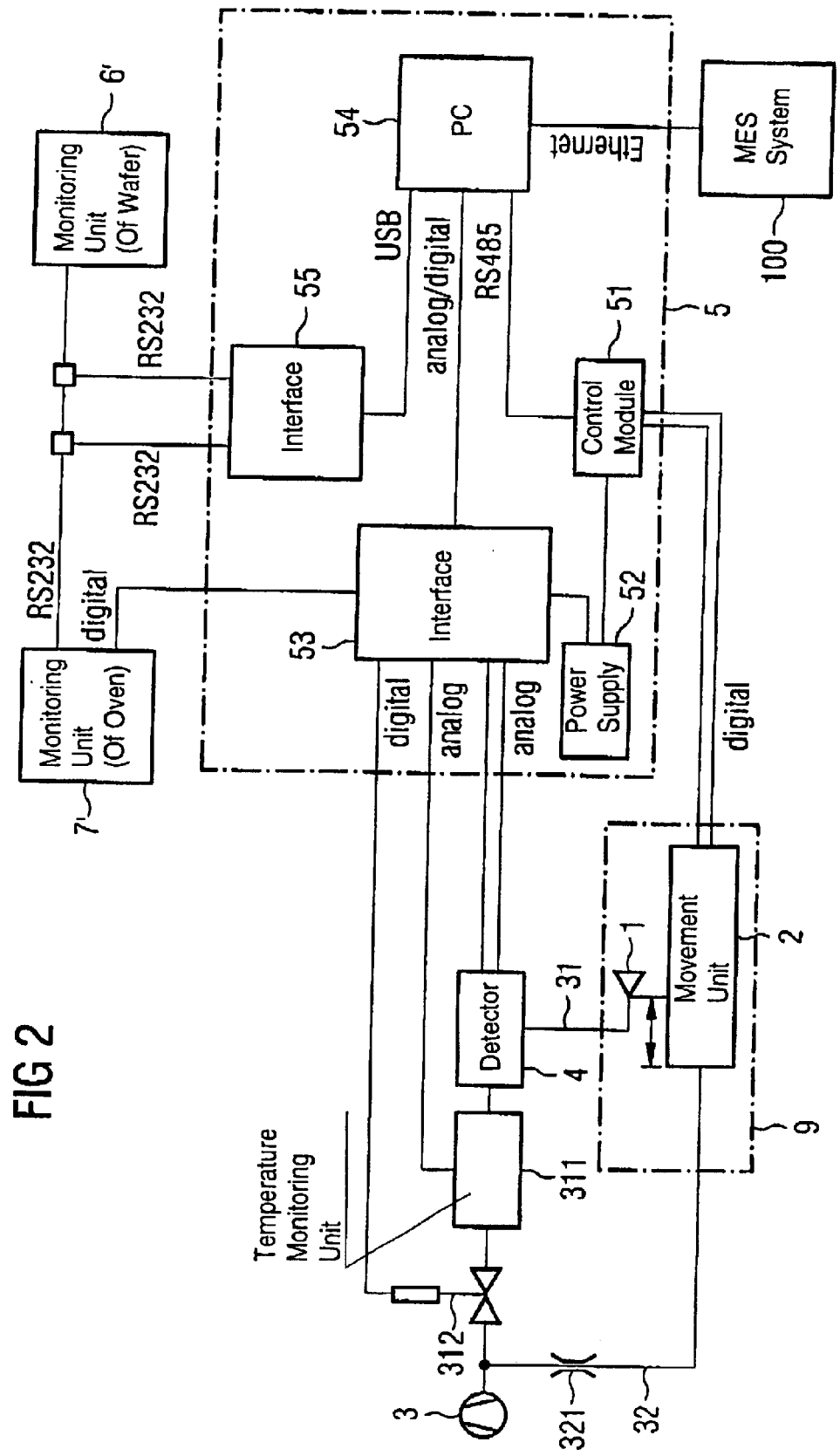
FIG. 2 is a diagram showing the interplay of components of an oven, according to an exemplary embodiment of the invention.

The control unit 5 of the probe 1 helps the vacuum pump 3 to take in air via the valve 312, so that an air sample from the loading and unloading areas 9 is led to the particle detector 4 via the aerosol line 31 (as shown in FIG. 2). According to the invention, the vacuum pump can also correspond to the service vacuum. The valve 312 and particle detector 4, which are fitted to the fabrication appliance 7 outside the loading and unloading area 9, are monitored via an interface 53 belonging to the control unit 5.

In this embodiment, a PC (personal computer) 54 forms the central unit of the control unit 5. The completion of the oven process is reported by the monitoring unit 7' of the oven 7 to the PC 54 via an interface 55. Within a period of 1 second, the particle detector 4 feeds back the reported particle numbers from the extracted air to the PC 54 via the interface 53. From this, the PC 54 calculates the number density, given the knowledge of the air volume extracted; a comparison with limiting values, which have been stored previously, is carried out.

If the boat 200 is already in the loading and unloading position (the bottom right position in FIG. 1), then at the start of wafer handling, a signal is sent to the PC 54 of the control unit 5 via the interface 55 by the monitoring unit 6' of the wafer handler 6. For the critical situation of possible contamination as well, the valve 312 for the vacuum pump 3 is activated via the interface 53 to suck air into the particle detector 4 via the probe 1. The position data from the wafer handler is transmitted with the signal sent by the monitoring unit 6'. As a result, the PC 54 causes the movement unit 2 (via the control module 51) to move the probe 1 into a movement position, which corresponds to the handler position and is stored in the PC 54. According to FIG. 1, this takes place along the movement rail 21 out of the plane of the drawing.

The vacuum pump 3 sucks air out of the interior of the movement unit 2, which is slightly encapsulated, via the flow-limiting nozzle 321 and the extraction line 32. As a result, a negative pressure is produced in the interior, which extracts particles produced by the drive and prevents the particles from the movement unit getting into the loading and unloading area.

The factory-wide MES system (Manufacturing Execution System) is connected to the PC 54 via a local network or via an Ethernet, so that the particle numbers or densities determined can be reported onward factory-wide.

FIG. 3 shows the time variation of the particle number density measurement. The output signal of the measured current intensity in milliampere is plotted against time. The particle detector measures particles by laser irradiation in the air stream; a classification of sizes in various channels can be made by the intensity of the scattering of light. The particle detector is able to detect particle sizes from 0.3 to 0.5 μm in a first channel and particle sizes of more than 0.5 μm in a second channel. Particle detectors with other channel numbers, for example 1 or 6 channels, are likewise possible.

The particle detector supplies a current output signal for each particle size channel (as is illustrated in the upper flowchart of FIG. 3). The signal is smoothed via a low-pass filter and averaged over a time step of 1 second to form an average current value $I(x, t_y)$ wherein x corresponds to the channel, y to the time step number. The current signal is converted into an actual particle number by a calibration performed in advance, for example during the installation of the configuration. The time axis of the graph begins with the signal sent from the monitoring unit 6' of the wafer handler 6 to the control unit 5, which identifies the start of an unloading action of a wafer. At this time, the measured particle density is at a level, which corresponds to the quiescent state in the mini environment. This level can be viewed as a base level, which, as standard, can be achieved as a minimum by the filter systems of the air cleaning system. In the fourth second, that is the fourth time step, of this embodiment, the number of contaminating particles detected increases sharply as a result of the wafer handling.

The particle number is summed and compared in the control unit 5, over 10 time steps (10 seconds as handling duration), depending on the channel, with a maximum permissible limiting value which, for example, has been obtained by a comparison with test wafers. If the value exceeds the limiting value, an alarm is triggered, which permits immediate fault analysis and rectification, for example readjustment of the wafer handler or replacement of the boat 200. After 8 seconds of wafer handling, the measured particle number density falls again to the base level, as shown in FIG. 3.

In the exemplary embodiment (as shown in FIG. 1), the probe 1 is aligned unidirectionally with the airflow source 8, so that isokinetic removal of air from the airflow 81 is possible. However, it is likewise possible to implement a probe opening orientation, which is rotated at an angle with respect to the main airflow. An appropriately modified air extraction system is then necessary, so that the particles that have flaked off and are carried along by the airflow 81 can still pass into the probe for measurement.

We claim:

1. A configuration for determining a concentration of contaminating particles in a loading and unloading chamber of an appliance for processing at least one disk-shaped object, the loading and unloading chamber having a reduced concentration of contaminating particles with respect to surroundings of the processing appliance, comprising:

at least one probe disposed in the loading and unloading chamber having an opening for removing at least one gas sample from the loading and unloading chamber;

a movement unit disposed in the loading and unloading chamber, said probe coupled to said movement unit movably in at least one direction;

a particle detector for counting the contaminating particles in the gas sample;

a vacuum pump having lines for conveying the gas sample from said probe to said particle detector; and a control unit connected to said particle detector and said movement unit.

2. The configuration according to claim 1, wherein said particle detector is fitted outside the loading and unloading chamber.

3. The configuration according to claim 1, wherein said movement unit contains at least one movement rail and a drive, and said probe is movable along said movement rail by said movement drive.

4. The configuration according to claim 3, wherein the loading and unloading chamber contains a handling appliance for conveying the at least one disk-shaped object.

5. The configuration according to claim 4, wherein said handling appliance has a monitoring unit, and wherein said control unit is connected to said monitoring unit of said handling appliance for performing a particle density measurement during one of a loading and unloading activity of said handling appliance.

6. The configuration according to claim 4, wherein said handling appliance is a fabrication appliance for performing one of structuring, cleaning, layer-deposition and layer-processing of the surface of the disk-shaped object.

7. The configuration according to claim 6, wherein said fabrication appliance has a monitoring unit, and wherein said control unit is connected to said monitoring unit of said fabrication appliance for performing a particle number density measurement after a processing activity in said fabrication appliance.

8. The configuration according to claim 6, wherein said fabrication appliance is an oven for depositing a layer on the surface of the disk-shaped object at high temperatures.

9. The configuration according to claim 4, wherein said processing appliance is a sorting appliance for resorting disk-shaped objects from a first to a second disk transport container.

10. The configuration according to claim 4, wherein said probe is fixed to said handling appliance for conveying the at least one disk-shaped object.

11. The configuration according to claim 4, further comprising:

a disk carrier having sides disposed in the loading and unloading chamber, said disk carrier having at least one insertion space to accommodate the at least one disk-shaped object for a common processing of the objects in said fabrication appliance.

12. The configuration according to claim 11, wherein said disk carrier includes a configuration of insertion spaces along an axis having an overall extent, and wherein said linear movement rail is disposed parallel to the axis when said disk carrier is in one of a loading and unloading positions, said movement rail having a length at least as long as the overall extent of the axis.

13. The configuration according to claim 4, wherein the loading and unloading chamber contains a ventilation system having an airflow source for producing a substantially laminar airflow with a substantially reduced concentration of contaminating particles in the loading and unloading chamber, and wherein said probe is fitted to a side of the disk carrier facing away from said airflow source.

14. The configuration according to claim 13, wherein said sides include a lee side and wherein said probe is fitted to said lee side of said disk carrier in the loading and unloading chamber.

15. The configuration according to claim 13, wherein said opening of said probe points in the direction of said airflow source for removing an isokinetic gas sample.

16. The configuration according to claim 1, wherein the disk-shaped object is one of a semiconductor wafer, a mask, a reticle and a flat panel display.

17. The configuration according to claim 1, wherein said movement unit is at least partly covered by a thermally insulating covering for protection against heat.

18. The configuration according to claim 1, wherein said movement unit is connected to said vacuum pump via an extraction line for extracting particles produced by abrasion in said movement unit during driving.

19. A method of determining a density of contaminating particles in a loading and unloading chamber of a processing appliance for processing at least one disk-shaped object, the loading and unloading chamber having a reduced concentration of contaminating particles with respect to the surroundings of the processing appliance, which comprises the steps of:

provding the disk-shaped object in the loading and unloading chamber;

conveying the disk-shaped object with a handling appliance to a first position in the loading and unloading chamber;

transmitting the first position to a control unit of a probe;

moving the probe based on the first position with a movement unit to a second position in the loading and unloading chamber;

removing an air sample from the loading and unloading chamber with the probe at the second position;

conveying the air sample to a particle detector connected to the control unit;

measuring a number of particles in each volume element of the air sample with the particle detector;

comparing the number of particles with a threshold value; and generating a signal based on a result of the comparison.

20. The method according to claim 19, wherein the first position is an insertion space for the disk-shaped object in a disk carrier, and the second position for the probe lies on a side of the disk carrier facing away from an airflow source in the loading and unloading chamber on a lee side of the disk carrier.

21. The method according to claim 20, wherein the disk carrier is replaced on the basis of the signal.

22. The method according to claim 20, wherein the handling apparatus is adjusted on the basis of the signal.

23. The method according to claim 19, wherein the removing, conveying the air sample and measuring steps are repeated with a period of less than 5 seconds.

24. The method according to claim 19, which further comprises the step of generating a starting signal with the handling appliance, when the conveying step of the disk-shaped object is carried out, before a first measurement.

* * * * *